(12) United States Patent
 Walker

(10) Patent No.: US 7,966,196 B2
(45) Date of Patent: *Jun. 21, 2011

(54) SYSTEM AND METHOD FOR EARLY IDENTIFICATION OF SAFETY CONCERNS OF NEW DRUGS

(75) Inventor: Alexander M. Walker, Concord, MA (US)

(73) Assignee: Ingenix, Inc., Eden Prairie, MN (US)

( * ) Notice: Subject to any disclaimer, the term of this patent is extended or adjusted under 35 U.S.C. 154(b) by 24 days.

This patent is subject to a terminal disclaimer.

(21) Appl. No.: 12/398,575

(22) Filed: Mar. 5, 2009

(65) Prior Publication Data

US 2009/0157425 A1    Jun. 18, 2009

Related U.S. Application Data

(63) Continuation of application No. 11/377,628, filed on Mar. 16, 2008.

(60) Provisional application No. 60/674,958, filed on Apr. 25, 2005.

(51) Int. Cl.
  *G06Q 10/00* (2006.01)
(52) U.S. Cl. ............................................. 705/2; 705/4
(58) Field of Classification Search ........................ 705/2
  See application file for complete search history.

(56) References Cited

U.S. PATENT DOCUMENTS 5,845,255 A   12/1998 Mayaud
(Continued)

FOREIGN PATENT DOCUMENTS

GB    2310060 A    8/1997
(Continued)

OTHER PUBLICATIONS

Graham, David J., et al., "Incidence of Hospitalized Rhabdomyolosis in Patients Treated with Lipid-Lowering Drugs" (JAMA, Dec. 1, 2004, vol. 292, No. 21, pp. 2585-2590).

(Continued)

*Primary Examiner* — Gerald J. O'Connor
*Assistant Examiner* — Hiep V. Nguyen
(74) *Attorney, Agent, or Firm* — Devan V. Padmanabhan; Dorsey & Whitney LLP

(57) ABSTRACT

A computer-implemented system and method for administering a drug registry database generates a display of a plurality of new drug/comparator drug pairings, wherein each new drug is added to the database when a threshold number of healthcare claims for the new drug have been received. Upon receiving a selection of a new drug/comparator drug pairing, and filter parameters input by a user, an analysis engine searches the healthcare claims stored in the database to identify a first and second group of patients satisfying the filter parameters input by the user; wherein the first group includes patients with claim data indicating use of the new drug and the second group includes patients with claim data indicating use of the comparator drug. The analysis engine further identifies a comparative occurrence of one or more existing medical conditions or new medical conditions in the first and second groups of patients and calculates a probability value indicating a relative likelihood that a patient taking the new drug will have each of the one or more new or existing medical conditions in comparison to a likelihood that a patient taking the comparator drug will have each of the one or more new or existing medical conditions. A user interface displays each new or existing medical condition and the probability value for the new drug and the comparator drug in accordance with one or more report parameters entered by the user.

6 Claims, 10 Drawing Sheets

U.S. PATENT DOCUMENTS

| | | | |
|---|---|---|---|
| 6,219,674 B1 * | 4/2001 | Classen | 1/1 |
| 6,529,892 B1 * | 3/2003 | Lambert | 706/55 |
| 6,584,472 B2 | 6/2003 | Classen | |
| 7,461,006 B2 | 12/2008 | Gogolak | |
| 2002/0083080 A1 | 6/2002 | Classen | |
| 2002/0183965 A1 | 12/2002 | Gogolak | |
| 2003/0046110 A1 | 3/2003 | Gogolak | |
| 2005/0079511 A1 | 4/2005 | Mandema et al. | |
| 2006/0111847 A1 | 5/2006 | Pearson et al. | |
| 2006/0195418 A1 | 8/2006 | Classen | |
| 2007/0033075 A1 * | 2/2007 | Hoffman et al. | 705/3 |

FOREIGN PATENT DOCUMENTS

| | | |
|---|---|---|
| WO | WO 02/088901 A2 | 11/2002 |
| WO | WO 02/089015 A1 | 11/2002 |
| WO | WO2005031509 | 4/2005 |

OTHER PUBLICATIONS

Geraud, G., et al., "Tolerability and safety of frovatripan with short- and long-term use of treatment of migraine and in comparison with sumatripan" (Headache, Apr. 2002, 42 Suppl. 2:S93-9).

Layton, Deborah, et al. "Is there an association between selective serotonin reuptake inhibitors and risk of abnormal bleeding?" (Eur. J. Clin. Pharmacol. (2001) 57: 167-176).

Enger, Cheryl, et al. "Serious ventricular arrhythmias among users of cisapride and other QT-prolonging agents in the United States" (Pharmacoepidemiology and Drug Satety 2002; 11: 477-486).

Walker, "Pattern recognition in health insurance claims databases," *Pharmacoepidemiology and Drug Safety*, 2001; 10: 393-397.

Smalley et al., "Contraindicated Use of Cisapride: Impact of Food and Drug Administration Regulatory Action," *Journal of the American Medical Association*, vol. 284, No. 23 (Dec. 20, 2000). 3036-3039.

Walker et al., "Patterns of Interchange in the Dispensing of Non-Steroidal Anti-Inflammatory Drugs," *J. Clin. Epidemiol.*, vol. 45, No. 2 (1992). 187-195.

Jick et al., "Postmarketing Follow-up," *Journal of the American Medical Association*, vol. 242, No. 21 (Nov. 23, 1979). 2310-2314.

* cited by examiner

Fig. 3

Example Table

| Experience | New Drug Patient Group | Comparator Drug Patient Group | P Value |
|---|---|---|---|
| • Myocardial Infarction | 2 / 1000 | 4 / 25,672 | 0.001 |
| • High Blood Pressure | 23 / 1000 | 147 / 25,672 | 0.012 |
| • High Cholesterol | 37 / 1000 | 377 / 25,672 | 0.024 |
| • Stroke | 5 / 1000 | 123 / 25,672 | 0.0004 |

FIG. 5

Drug/Comparator Lookup

| Drug/Comparator | Report Access | Data Mining | Data Download |
|---|---|---|---|
| Spiriva/Atrovent | 📄 | ® | 📁 |
| Ketek/Biaxin | 📄 | ® | 📁 |
| Cymbalta/Effexor | 📄 | ® | 📁 |
| Cialis/Viagra | 📄 | ® | 📁 |
| Levitra/Viagra | 📄 | ® | 📁 |
| Lunesta/Ambien | 📄 | ® | 📁 |
| Crestor/Lipitor | 📄 | ® | 📁 |
| Elestat/Patanol | 📄 | ® | 📁 |
| Ertaczo/Oxistat | 📄 | ® | 📁 |
| Factive/Levaquin | 📄 | ® | 📁 |
| Iressa/Non-Drug | 📄 | ® | 📁 |
| Reyataz/Kaletra | 📄 | ® | 📁 |
| Sanctura/Detrol | 📄 | ® | 📁 |
| Uroxatral/Flomax | 📄 | ® | 📁 |
| Vesicare/Detrol | 📄 | ® | 📁 |
| Xifaxan/Cipro | 📄 | ® | 📁 |

Records 1 - 16 of 16

FIG. 6

INSIGHTS ON DRUG SAFETY. FASTER.

HOME | PRINT | HELP | USER PROFILE | LOGOUT

Reports ▼ | ▽ Filters ▼ | Data Version ▼

Select Drug | Ketek/Biaxin Reports

Drug Comparator: Ketek/Biaxin
Earliest Possible Date of Dispensing: 07/01/2004
Latest Possible Date of Dispensing: 12/31/2004
Latest Possible Date for Follow-up: 04/30/2005

Standard Reports - Ketek/Biaxin

Report Name

Demographic Characteristics

Baseline Diagnoses

Baseline Procedures

Baseline Therapeutic Drug Class Dispensings

Baseline Healthcare Utilization

Characteristics of Prescribers

Treatment Patterns

Emergent Primary Inpatient Diagnoses

Emergent Outpatient Diagnoses

Emergent Other Diagnoses

Emergent Procedures

Emergent Therapeutic Drug Class Dispensings

Healthcare Utilization 1-3 months after Initiation

Healthcare Utilization 4-6 months after Initiation

Healthcare Utilization 7-9 months after Initiation

Healthcare Utilization 10-12 months after Initiation

Records 1 - 16 of 16

FIG. 8

INSIGHTS ON DRUG SAFETY. FASTER.
Reports ▼ | Filters ▼

HOME | PRINT | HELP | USER PROFILE | LOGOUT

Select Drug
Add Filtered View

Filter Name:

Days since first dispensing:
--Not Specified--

Drug/Comparator:
--Not Specified--

Report:
--Not Specified--

Age Groups:
☐ 0 - 9
☐ 10 - 19
☐ 20 - 29
☐ 30 - 39
☐ 40 - 49
☐ 50 - 59
☐ 60 - 64
☐ 65 +

Drug Classes:
◉ Include ○ Exclude
[ Add... ]
[ Remove ]

Genders:
☐ Female
☐ Male

Diagnosis Codes:
◉ Include ○ Exclude
[ Add... ]
[ Remove ]

Regions:
☐ Northeast
☐ Midwest
☐ South
☐ West

Procedure Codes:
◉ Include ○ Exclude
[ Add... ]
[ Remove ]

☐ Share this filter?

[ Save ]  [ Preview ]  [ Cancel ]

FIG. 9A i3Aperio™
Drug Experience Registry

INSIGHTS ON DRUG SAFETY. FASTER.

HOME | PRINT | HELP | US

Reports ▼ | ▼ Filters ▼ | Data Version ▼

Select Drug | Data Mining - Outpatient Diagnosis

Drug Comparator: Ketek/Biaxin
Report: Data Mining - Outpatient Diagnosis
Earliest Possible Date of Dispensing: 07/01/2004
Latest Possible Date of Dispensing: 12/31/2004
Latest Possible Date for Follow-up: 04/30/2005

Data Mining - Outpatient Diagnosis of Ketek/Biaxin - 07/01/2004 - 12/31/2004

| Attribute ⇅ | Attribute Type ⇅ | Attribute Description ⇅ | Outcome Class ⇅ | Outcome Type ⇅ | Outcome Description ⇅ | Ketek | | Biaxin | | RR ⇅ | RR Lower ⇅ | RR Upper |
|---|---|---|---|---|---|---|---|---|---|---|---|---|
| | | | | | | Events ⇅ | N ⇅ | Events ⇅ | N ⇅ | | | |
| Baseline | | | DX_OUTPATIENT | 471 | Nasal polyps | 88 | 22,453 | 38 | 22,453 | 2.3 | 1.6 | 3.4 |
| PX Baseline | 231 | Other Therapeutic Procedure | DX_OUTPATIENT | 473 | Chronic sinusitis | 311 | 4,382 | 221 | 4,308 | 1.4 | 1.2 | 1.6 |
| PX Baseline | 197 | Other Diagnostic Ultrasound | DX_OUTPATIENT | 611 | Other disorders of breast | 11 | 1,609 | 40 | 1,673 | 0.3 | 0.1 | 0.6 |
| DX Baseline | 702 | Other dermatoses | DX_OUTPATIENT | 472 | Chronic pharyngitis and nasopharyngitis | 29 | 595 | 7 | 608 | 4.2 | 1.8 | 10.6 |
| DX Baseline | 381 | Nonsuppurative otitis media and Eustachian tube disorders | DX_OUTPATIENT | 536 | Disorders of function of stomach | 0 | 659 | 13 | 621 | 0.0 | 0.0 | 0.4 |
| Baseline | | | DX_OUTPATIENT | V70 | General medical examination | 1,030 | 22,453 | 1,196 | 22,453 | 0.9 | 0.8 | 0.9 |
| GENDER | F | | DX_OUTPATIENT | 461 | Acute sinusitis | 1,149 | 13,884 | 994 | 13,812 | 1.1 | 1.1 | 1.3 |
| Baseline | | | DX_OUTPATIENT | 473 | Chronic sinusitis | 1,113 | 22,453 | 948 | 22,453 | 1.2 | 1.1 | 1.3 |
| GENDER | M | | DX_OUTPATIENT | 477 | Allergic rhinitis | 628 | 8,569 | 530 | 8,641 | 1.2 | 1.1 | 1.3 |
| RX Baseline | | Nasal anti-inflammatory steroids | DX_OUTPATIENT | 461 | Acute sinusitis | 314 | 3,071 | 229 | 2,944 | 1.3 | 1.1 | 1.6 |

FIG. 9B perio
Drug Experience Registry

N DRUG SAFETY FASTER.

▼ | ▼ Filters ▼ | ▦ Data Version ▼

HOME | PRINT | HELP | USER PROFILE | LOGOUT

Data Mining - Outpatient Diagnosis rator: Ketek/Biaxin
Mining - Outpatient Diagnosis
ible Date of Dispensing: 07/01/2004
ole Date of Dispensing: 12/31/2004
ole Date for Follow-up: 04/30/2005

- Outpatient Diagnosis of Ketek/Biaxin - 07/01/2004 - 12/31/2004

| Attribute Type ⇕ | Attribute Description ⇕ | Outcome Class ⇕ | Outcome Type ⇕ | Outcome Description ⇕ | Ketek Events ⇕ | Ketek N ⇕ | Biaxin Events ⇕ | Biaxin N ⇕ | RR ⇕ | RR Lower ⇕ | RR Upper ⇕ | Score ⇕ |
|---|---|---|---|---|---|---|---|---|---|---|---|---|
| 231 | Other Therapeutic Procedure | DX_OUTPATIENT | 471 | Nasal polyps | 88 | 22,453 | 38 | 22,453 | 2.3 | 1.6 | 3.4 | 5 |
| 197 | Other Diagnostic Ultrasound | DX_OUTPATIENT | 473 | Chronic sinusitis | 311 | 4,382 | 221 | 4,308 | 1.4 | 1.2 | 1.6 | 4 |
| 702 | Other dermatoses | DX_OUTPATIENT | 611 | Other disorders of breast | 11 | 1,609 | 40 | 1,673 | 0.3 | 0.1 | 0.6 | -4 |
| 381 | Nonsuppurative otitis media and Eustachian tube disorders | DX_OUTPATIENT | 472 | Chronic pharyngitis and nasopharyngitis | 29 | 595 | 7 | 608 | 4.2 | 1.8 | 10.6 | 4 |
|  |  | DX_OUTPATIENT | 536 | Disorders of function of stomach | 0 | 659 | 13 | 621 | 0.0 | 0.0 | 0.4 | -4 |
|  |  | DX_OUTPATIENT | V70 | General medical examination | 1,030 | 22,453 | 1,196 | 22,453 | 0.9 | 0.8 | 0.9 | -3 |
| F |  | DX_OUTPATIENT | 461 | Acute sinusitis | 1,149 | 13,884 | 994 | 13,812 | 1.1 | 1.1 | 1.3 | 3 |
|  |  | DX_OUTPATIENT | 473 | Chronic sinusitis | 1,113 | 22,453 | 948 | 22,453 | 1.2 | 1.1 | 1.3 | 3 |
| M |  | DX_OUTPATIENT | 477 | Allergic rhinitis | 628 | 8,569 | 530 | 8,641 | 1.2 | 1.1 | 1.3 | 3 |
| Nasal anti-inflammatory steroids |  | DX_OUTPATIENT | 461 | Acute sinusitis | 314 | 3,071 | 229 | 2,944 | 1.3 | 1.1 | 1.6 | 3 |

SYSTEM AND METHOD FOR EARLY IDENTIFICATION OF SAFETY CONCERNS OF NEW DRUGS

PRIORITY CLAIM

This application is a continuation of U.S. patent application Ser. No. 11/377,628, filed Mar. 16, 2006, and claims the benefit of U.S. Provisional Application No. 60/674,958, filed on Apr. 25, 2005. The contents of both of these applications are hereby incorporated by reference in their entirety.

FIELD OF THE INVENTION

This invention relates, in general, to data processing techniques, and more specifically to analyzing healthcare data.

BACKGROUND OF THE INVENTION

During the last decade, the prescription drug approval period has been shortened and the number of drugs receiving approval has risen. While most of these drugs are safe, the emergence of information sufficient to prompt a safety recall often does not take place before widespread usage of the drug by a large patient population over many months or years. In other words, some safety issues do not become apparent until after a drug has been taken by a large patient population over a period of time.

As recognized by the present inventors, what is needed is a method and system for early identification of safety concerns of new drugs.

SUMMARY

In light of the above and according to one broad aspect of one embodiment of the present invention, disclosed herein is a method for identifying safety concerns regarding a new drug. In one example, the method utilizes a database of healthcare claims. The method may include identifying from the database a first group of patients that have received the drug; extracting one or more medical events that the first group of patients have experienced; identifying a second group of patients that have received a comparator drug; extracting one or more medical events that the second group of patients have experienced; and comparing the one or more medical events of the first group to the one or more medical events of the second group to determine one or more common occurrences therebetween.

Generally, the comparator drug is selected to have the same or similar pharmacological purpose as the new drug and the comparator drug will generally have been on the market for a greater period of time than the new drug.

The method may also include computing a probability value for each of the one or more common occurrences. In this way, embodiments of the present invention may be used to identify and quantify the probability that certain medical events will occur to patients taking the new drug.

The method may also employ various filters if desired, including for example filtering the one or more common occurrences based on ages of the first and second group of patients; filtering the one or more common occurrences based on genders of the first and second group of patients; filtering the one or more common occurrences based on one or more diagnosis codes of the healthcare claims of the first and second group of patients; filtering out pre-existing conditions from the one or more common occurrences of the healthcare claims of the first and second group of patients.

In another example, the method may also include determining whether the drug has been prescribed in an amount exceeding a minimum threshold, such as 1,000 patients for example.

According to another broad aspect of another embodiment of the present invention, disclosed herein is a system comprising a database of healthcare claims and an engine for identifying safety concerns regarding a new drug. The engine may be implemented as a computer program or process running on a computer or server. In one example, the engine includes a module for identifying from the database a first group of patients that have received the drug; a module for extracting from the database one or more medical events that the first group of patients have experienced; a module for identifying from the database a second group of patients that have received a comparator drug; a module for extracting from the database one or more medical events that the second group of patients have experienced; and a module for comparing the one or more medical events of the first group to the one or more medical events of the second group to determine one or more common occurrences therebetween.

Depending upon the implementation, the engine may perform various functions, such as computing a probability value for each of the one or more common occurrences; filtering the one or more common occurrences based on ages of the first and second group of patients; filtering the one or more common occurrences based on genders of the first and second group of patients, and other operations or functions disclosed herein.

The features, utilities and advantages of the various embodiments of the invention will be apparent from the following more particular description of embodiments of the invention as illustrated in the accompanying drawings.

BRIEF DESCRIPTION OF THE DRAWINGS

FIG. 3 illustrates an example of a table that can be used to display results include the probability that a patient receiving the new drug will experience a medical event or condition, in accordance with one embodiment of the present invention.

FIG. 5 illustrates an exemplary computer display screen providing a listing of drugs for selection as the new drug or as the comparator drug in accordance with one embodiment of the present invention.

FIG. 6 illustrates an exemplary computer display screen providing a report selection window in accordance with one embodiment of the present invention.

FIG. 8 illustrates an exemplary computer display screen providing selectable filter parameters in accordance with one embodiment of the present invention.

FIGS. 9A and 9B illustrate an exemplary computer display screen of data mining processes in accordance with one embodiment of the present invention.

DETAILED DESCRIPTION

Embodiments of the present invention provide various methods (as well as computer implementations) for early identification of drug safety concerns based on medical claims data. Various embodiments of the present invention are described herein.

Figure 1:
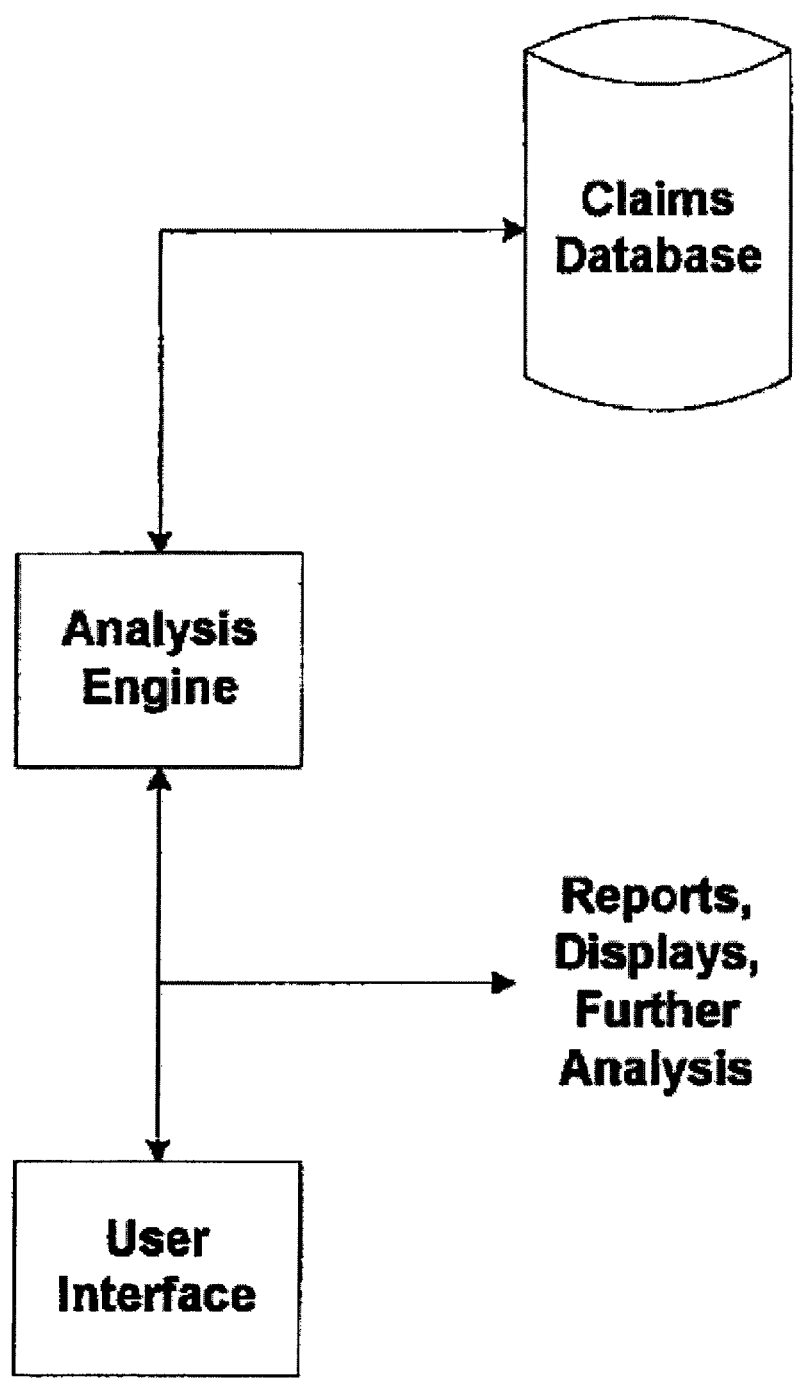
FIG. 1 illustrates an example of a block diagram for identifying and analyzing safety concerns regarding new drugs, in accordance with one embodiment of the present invention.

FIG. 1 illustrates a block diagram of one embodiment of the present invention. In one example, a conventional health care claims database is utilized which contains claims, including procedure code descriptions, such as a CPT code, for each claim line item. The claims data may also include ICD-9 codes, which are an International Classification of Disease indicating why a particular procedure or medical service was performed, also known as a "diagnosis" codes.

An analysis engine is provided for analyzing data from the claims database in order to provide for early identification of safety concerns for new drugs. A user interface may be provided to the analysis engine so that a user can perform analysis to identify potential safety concerns for specific new drugs, and generate reports, displays, etc. Further analysis may be conducted by the user in various manners, as disclosed herein. The analysis engine may perform one or more of the operations described herein for analyzing the data in the claims database for early identification of safety concerns for new drugs.

Figure 2:
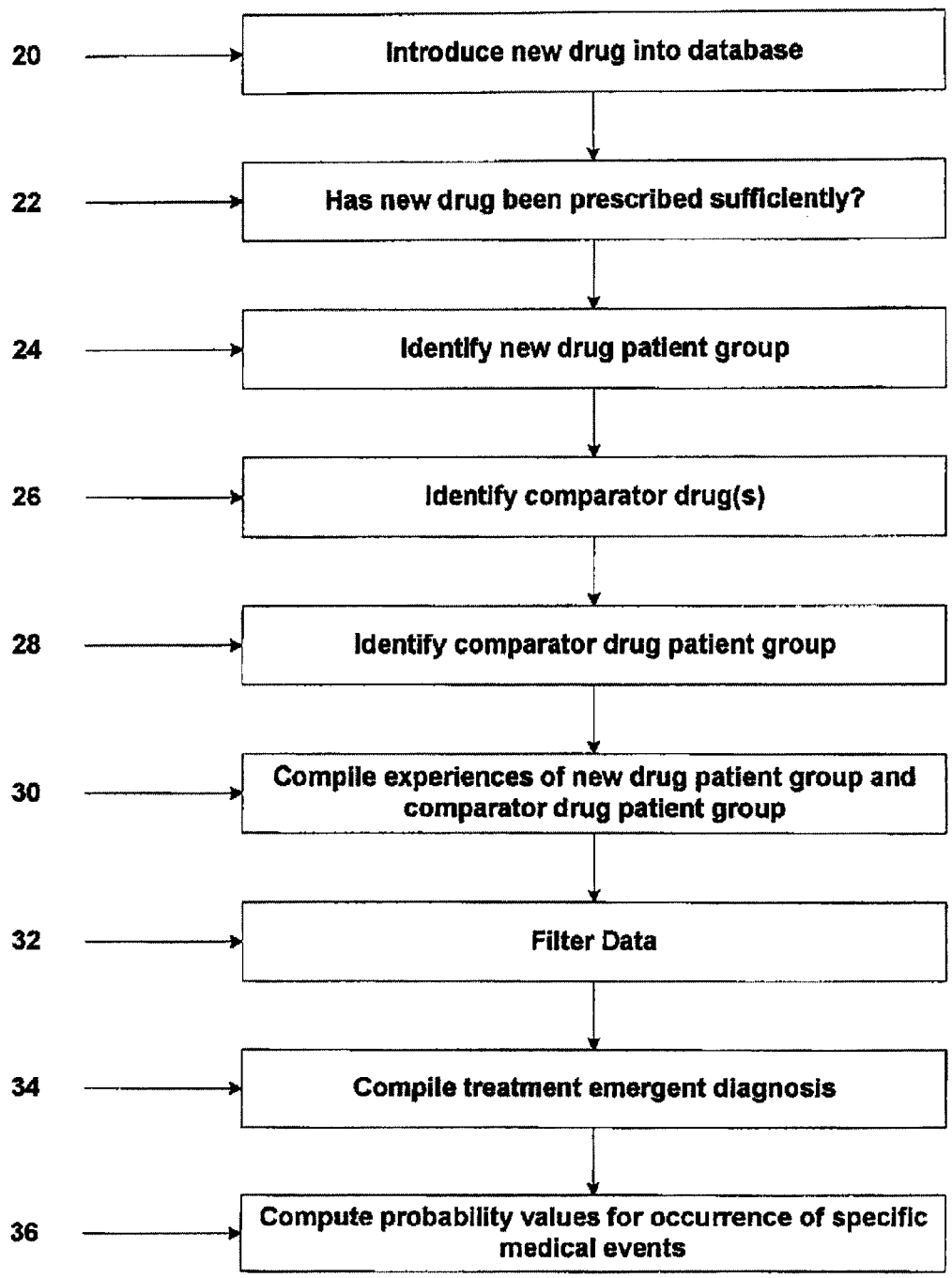
FIG. 2 illustrates an example of operations for identifying safety concerns regarding new drugs, in accordance with one embodiment of the present invention.

FIG. 2 illustrates an example of operations for early identification of safety concerns for new drugs, in accordance with one embodiment of the present invention. At operation 20, a new drug is identified as one that will be tracked using a claims database, for purposes of tracking users' experiences with the new drug. In one example, the database includes data from healthcare claims, including IDC9 codes and pharmacological codes. These codes are well known in the art and are associated with specific diagnoses and treatments that patients receive from treating physicians as reported to medical insurance companies.

At operation 22, the number of patients prescribed the new drug is monitored or checked to see if that number has exceeded a threshold. In one example, operation 22 determines whether the new drug has been prescribed to more than 1,000 patients. It is understood that different thresholds can be utilized depending upon the implementation. Once the drug has been prescribed to a number of patients exceeding the threshold, then operation 22 passes control to operation 24.

At operation 24, a new drug patient group is identified from the claims database. In one example, the claims database is searched for all patients that have been prescribed the new drug, and for each patient that has been prescribed the new drug, all data relating to that patient in the claims database is extracted and stored in a data file or other data structure. This data may include the medical experience of each of the patients that have been prescribed the new drug, including the IDC9 and CPT code data for those patients which may include events, symptoms, and other data relating to the patients and their medical experiences.

At operation 26, a comparator drug is identified. In a broad sense, a comparator drug may include a drug similar to or prescribed for a similar purpose as the new drug. The comparator drug generally may be characterized as being a more mature drug in the marketplace, for instance, the comparator drug may have been FDA approved and prescribed by physicians in the ordinary course of treating patients. In one example, a comparator drug is selected manually based on similar characteristics between the comparator drug and the new drug. In another example, a propensity score is generated to assist in the selection of a comparator drug.

At operation 28, having identified a comparator drug at operation 26, a comparator drug patient group is identified. Operation 28 may include extracting claims data from the claims database for each person that has been prescribed the comparator drug. Statistical analysis can be performed upon this patient data to help refine the group of users of the comparator drug. Once the comparator drug patient group has been selected, the experiences of the patients of the comparator drug patient group may be extracted from the claims database and stored in a file or other data structure.

At operation 30, the experiences of the new drug patient group and the comparator drug patient group are compiled. Operation 30 compiles these experiences based on the IDC9 code data or other claims data gathered by operations 24 and 28.

Operation 30 may compare the data from the new drug patient group to the comparator drug patient group in order to determine, statistically, the frequency of common occurrences between the patient groups. This data may be expressed in a table or other representation in a number of forms. In one example, a table may be created (such as shown in FIG. 3), wherein a column represents the experiences of patients who use the new drug, another column represents the experiences of patients who use the comparator drug, and a third column may indicate the adjusted "p value" which indicates the probability that certain experiences may occur based upon usage of the new drug.

At operation 32, the data for the new drug patient group and the comparator drug patient group may be filtered in various manners. In one example, for each patient, the date at which the patient was prescribed either the new drug (or the comparator drug) is identified, and the filtering process may include identifying symptoms that the patient had prior to the prescription of the new drug (or the comparator drug). In effect, this filtering operation identifies pre-existing conditions prior to the prescription of the new drug (or the comparator drug) for a particular patient. This pre-existing condition data can then be filtered out or excluded from the analysis, if desired.

At operation 34, the medical experiences of the patients after the date of their prescriptions of the new drug (or comparator drug) can be analyzed. For instance, in one example, the conditions that exist twelve months after a patient has been prescribed the new drug (or comparator drug) may be compiled in order to determine whether such medical conditions are common to users of the comparator drug and of the new drug within the first twelve months after prescription. This treatment emergent diagnosis helps identify and statistically analyze the codes/medical conditions that occur after user of either the new or comparator drug.

At operation 36, a probability "p value" is computed for each possible medical experience based on the data previously compiled and analyzed. Operation 36, in effect, calculates a "p value" for certain medical events or symptoms, and in this way, operation 36 can statistically quantify the probability that a patient taking the new drug may experience a particular medical event or symptom. Operation 36 may utilize conventional data mining techniques for statistical calculations in order to account for irrelevant or statistically insignificant occurrences.

Upon computing the probability "p value" for statistically significant medical event or symptom potentially associated with use of the new drug, this data can be incorporated into a table or other form for reports or displays. FIG. 3 illustrates an example of a table that may be created based upon one or more operations disclosed herein. It is understood that FIG. 3 is provided by way of example only, and is not intended to limit the scope of the present invention.

As shown in FIG. 3, the columns of the table include the medical experience type (such as conditions, symptoms or events or other experiences), and for the new drug patient group, a column indicating the number of occurrences of the particular experience along with the number of patients in the new drug group. Another column may be provided which shows, for the comparator drug patient group, the number of occurrences of the particular experience, along with the number of patients in the comparator drug patient group. For each particular experience, a probability or "p value" may be calculated and displayed. Note that the values provided in this example table of FIG. 3 are not based upon actual calculations, but rather are merely example fictitious numbers provided only for the purpose of illustrating how data may be arranged and displayed.

For instance, from the example table, it can be seen that the number of occurrences of high cholesterol for the new drug patient group was 37 out of 1,000, and for the comparator drug patient group, the number of occurrences was 377 out of 25,672. A "p value" for high cholesterol is illustrated as 0.024 in this hypothetical example.

In accordance with one embodiment of the present invention (not shown), p-values may be used for internal calculations, while a simpler numerical value derived from the p-value is displayed by the system. For example, the following conversion may be used:

| p-value range | displayed score |
|---|---|
| >0.10 | 0 |
| ≦0.10 and >0.01 | 1 |
| ≦0.01 and >0.001 | 2 |
| ≦0.001 and >0.01 | 3 |

Additional values may be calculated using the same methodology. Also, the sign of the displayed score may be adjusted to be positive when there are more events for the new drug than for the comparator and negative when there are fewer events for the new drug than for the comparator.

Figure 4:
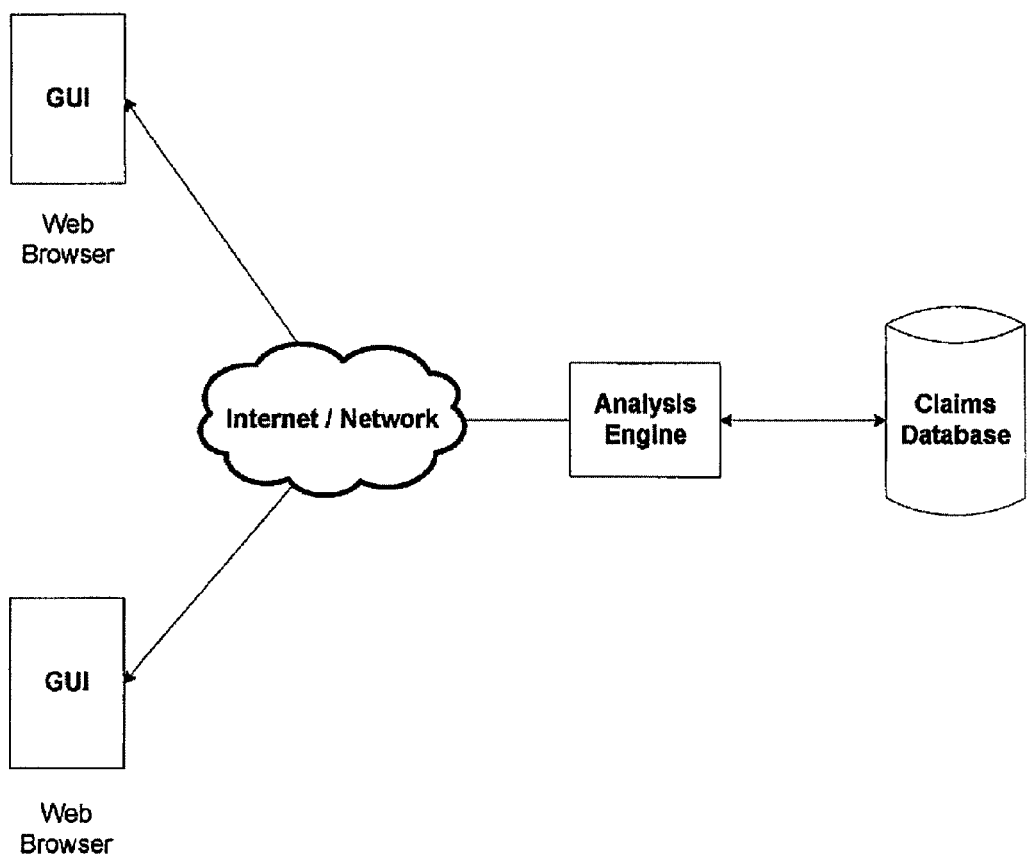
FIG. 4 illustrates another example of a block diagram for identifying and analyzing safety concerns regarding new drugs, in accordance with one embodiment of the present invention.

Embodiments of the present invention may be implemented in a computing system or in a network based client server or ASP model. As shown in FIG. 4, a web-based interface can be provided so that users in various remote locations can perform the analysis of the data to identify safety concerns for new drugs. For instance, using an internet based system, graphical user interfaces can be provided to the users which provide the users (such as drug companies or governmental agencies) with the ability to further analyze the results of the data. For instance, analysis can be done which further analyzes or focuses on categories such as men older than 65, men older than 65 that are also using another third drug, etc.

In another embodiment of the present invention, a drug registry is created and provided. In one example, a drug registry may be an information product that will provide early information on the health care experience of people taking new drugs in the United States or other countries. The drug registry may use data including a robust cross section of people, and can link patient and physician data, pharmacy and medical claims data, and lab and diagnostic test results.

The drug registry can provide faster access to data to help researchers assess the relative risks of prescribed drugs, and in other embodiments, can provide access to integrated medical and prescription claims information on prescription drugs introduced on the market for which claims for reimbursement have been submitted. Due to the volume of experiences that are reflected in the database, even a drug prescribed in moderate volumes will likely be reflected in enough data to perform meaningful analysis.

In one example, the drug registry can help those responsible for drug safety make more timely and evidence-based decisions. In the last decade, more than 300 new prescription drugs were launched and the prescription drug approval period has been shortened. In addition, pharmaceutical and biotechnology companies are investing record amounts in research and development to bring more prescription drugs to market—in 2004, the industry invested $38.8 billion in R&D. But once clinical trials are completed and a drug is on the market, the emergence of information sufficient to prompt a safety recall often does not take place before widespread usage of the drug by a large patient population over many months or years. Embodiments of the present invention can help organize a large and growing source of health experience data in ways that may enable faster detection of significant trends.

The drug registry may be created and used to provide faster access to data to help researchers assess the relative risks of a prescribed drug. The drug registry can be a resource that large health plans, pharmaceutical companies, regulatory agencies like the U.S. Food and Drug Administration (FDA), and other stakeholders can use to review health care data relating to prescription drug use in a timely and objective manner. In addition, the results of the analysis of this data may ultimately help physicians write prescriptions with greater confidence, and allow patients to take new medications with added comfort and security. Such data may help researchers detect potentially significant trends earlier in a drug's market experience.

In one example, a drug registry may include a review of claims data generated by selected health plans. New molecular entities ("NMEs"—newly introduced drugs based on an innovative chemical structure) will enter the Registry as soon as 1,000 individuals in a health plan have received (i.e. filled a prescription) the drug. A comparison group of users of an established therapy with the same indications will be created. Through statistical matching, the two groups, NME and comparator, will have nearly identical demographic characteristics and health insurance experience. In one example, the two groups will have, within statistical precision, the same distribution over categories of age, sex, geographic region, diagnoses, drugs dispensed, procedures performed, and generalists and specialists seen. Within these groups, the drug registry may track the occurrence of medical conditions—both existing and new.

Proper selection of the comparator reference group of persons not receiving the NME will permit the drug registry to distinguish the distinct effect (good or bad) of an NME on the occurrence of complications that affect all drugs in a class, such as for example deep vein thrombosis in oral contraceptive users. The comparator group will also filter out many new diagnoses that represent the natural progression of the disease being treated, such as visual disorders in diabetics.

In one example, two groups of users are identified—users of established therapies, and users of newly introduced drugs—with both groups featuring closely matched demographic characteristics (e.g., age, sex, geographic region, diagnoses, drugs dispensed, procedures performed, etc.). Within these groups, the drug registry can offer data that may help researchers track the comparative occurrence of existing and new medical conditions.

By using a comparator, better benchmarking of a new drug can be realized with a view toward its patient population and the particular health issues typical of those patients. In addition, the comparator provides validation; it attempts to level the playing field to confirm that the symptoms showing are in fact true and are not an idiosyncrasy due to upcoding or some other claims issue.

Focusing on new diagnoses will aid the drug registry in solving the "forest and trees" problem—how to separate out new drug effects from the welter of ongoing conditions that were present before patients began using the NME.

Data mining—the use of sophisticated search algorithms to identify patterns of newly emergent conditions that might otherwise have escaped notice—may also be employed.

For example, a data mining algorithm may be employed to systematically evaluate the frequency of treatment-emergent codes among the NME group and the comparator group in subgroups of patients to detect if pronounced imbalance of the occurrence of codes existed in specific subgroups. As there is no a priori assumption about predefined subgroups, this process is referred to as data mining.

The data mining algorithm is described as follows:

Baseline attributes that are evaluated in data mining include: age group, sex, geographic region, diagnoses codes (3-digit level, inpatient, outpatient physician, or mental health professional, the same definition used in the baseline diagnosis table), procedure codes (AHRQ group level), drugs (therapeutic class level).

Outcomes that are evaluated in data mining include: treatment emergent inpatient primary diagnosis (ICD-9 codes at 3-digit level), treatment emergent outpatient visit diagnosis (ICD-9 codes at 3-digit level), and treatment emergent therapeutic drug class. Procedures for first level data mining include the following calculations:

$N_d$: number of subjects in the NME group in each cohort or subcohort $N_c$: number of subjects in the comparator group in each cohort or subcohort $x_d$: number of subjects in the NME group who had the treatment-emergent code $x_c$: number of subjects in the comparator group who had the treatment-emergent code $x_d + x_c = x$ (total number of emergent events)

$N_c + N_d = N$ (total number of matched NME and comparator drug initiators)

Score calculation:

If $x_d = x^* N_d/N$, then score=0

If $x_d < x^* N_d/N$, then score=$\log_{10}$(cumulative hypergeometric($x_d, N_d, x, N$))

If $x_d > x^* N_d/N$, then score=$-\log_{10}$(cumulative hypergeometric($x-x_d, N-N_d, x, N$))

(Scores may be truncated to integer values for presentation.)

Once the calculations and scores have been calculated as described above, the algorithm:

(1) calculates a score for each row for each of the outcome tables at the crude levcalculates a score for each row for each of the outcome tables at the crude level (i.e., the full NME cohort and comparator cohort);

(2) identifies all rows in which the absolute value of the score was 3 or more;

(3) restricts the two cohorts to those that have a certain baseline attribute, one at a time, for example, starting from age 0-9 through 65+, then proceeding to men, women, northeast, Midwest, south, west, ICD-9 code 001 through 999, each E code, each V code, all procedure codes, and all drug classes;

(4) skips subsets in which $N_d \leq 3$ or $N_c \leq 3$ or both;

(5) within a subset, evaluates each row in each outcome table, one at a time, such that rows satisfying the following criteria are kept: $(x_d + x_c) > 3$ and $((N_d + N_c) - (x_d + x_c)) > 3$;

(6) apply the following quadratic filter (e.g., in Oracle) to each row, keeping rows that fulfill this condition:

$$POWER(ABS(x_d - (x_d + x_c) * N_d/(N_d + N_c)) - 0.5, 2) \geq (4 * (x_d + x_c) * N_d/(N_d + N_c) * (1 - N_d/(N_d + N_c)))$$

(7) for all eligible rows in each table, calculate the score as described above;

(8) for each row, compare the score in the subset and the score in the full cohort and identify the subset and the row for which the absolute value of the score in the subset is larger than the absolute value of the score in the full cohort;

(9) for the subset and row combinations identified in steps (2) and (8) above, output the combinations for which the absolute value of the score was 3 or more to the Data Mining Output tables (see FIGS. 9A and 9B below).

In addition to data mining at the full cohort level, the algorithm described above in steps (1) through (9) may be applied to a defined subgroup. For example, a user may specify that Data Mining is to be applied to all men. In this case, at step (3), all attributes other than "sex" will be evaluated. Similarly, for data mining in the subgroup "age 40 or older," at step (3) all attributes other than "age" will be evaluated.

Other types of data mining algorithms may also be implemented in the system and method according to the present invention.

Drug withdrawals and labeling changes commonly occur following years of accumulation of patient experience. Embodiments of the present invention can complement existing safety monitoring techniques, which now consist primarily of doctor and patient reports and occasional dedicated surveillance programs mandated by the FDA. By greatly adding to the flow of relevant safety data, a drug registry in accordance with the present invention can support earlier identification of safety signals and earlier action.

Such a drug registry can offer researchers the data to analyze real-world prescription drug 30 experience, including the health experiences of patients with co-morbidities, or those taking multiple medications. Further, the registry can provide a much greater scope of data, which may allow researchers to identify more rare side effects that did not surface in prior analysis.

In one example, the drug registry can provide integrated medical and prescription claims information on drugs introduced since 2004 or earlier (or any prescription drug on the market can be studied), for which claims for reimbursement have been submitted. Due to the volume of experiences that are reflected in databases, even a drug prescribed in moderate volumes will likely be reflected in enough data to perform meaningful analysis.

In one example, the resulting drug registry information will be available in two formats: quarterly, web-based files suitable for manipulation and analysis by informed users, as well as an annual report of static data. Several product options, both online and print, may be provided. These range from annual comprehensive publications, to subscription services with rapid access to advanced analytics and querying capabilities, to a hard copy annual report that could serve as a key desk-side resource to pharmacy and therapeutic committees and hospital formulary committees. An annual report of all drugs in the registry can also be provided. Manufacturers may opt for more detailed information about how their drug is being used in the marketplace.

The registry can benefit a wide range of industry stakeholders. The registry will benefit a wide range of industry stakeholders, including pharmaceutical and biotech companies, investment firms, managed care organizations, government entities, hospitals, advocacy groups, and large employers In certain embodiments, the drug registry may:

Allow researchers to quantify already-known side effects to help physicians make therapeutic decisions about which drugs may be most appropriate for various patients Provide pharmaceutical manufacturers with a resource that can deliver value from R&D to commercialization Assist managed care organizations and large employers 25 with creation and updating of drug formularies Assist the government with regulatory and compliance decision-making Support prompt detection of critical safety issues, helping physicians and patients feel greater comfort and confidence in new medications The information in the drug registry can be made to be compliant with relevant HIPAA regulations.

One or more features of the present invention may be implemented utilizing various graphical user interfaces with various controls and displays of information to a user. FIGS. 5-9 illustrate example display screens, and one or more of these example display screens or portions thereof may be utilized when implementing embodiments of the present invention.

Generally, the graphical user interfaces may be arranged so as to provide the user with the ability to select a new drug and a comparator drug from a drug list; and to generate various reports by controlling or viewing various characteristics. For instance, reports may be viewed in tabular form and may include a variety of different standard reports, filtered views where the user may define characteristics of the views, and data mining of the filtered views may also be provided, Various filter parameters may be specified, in one example, such as filtering by the drug, age, gender, diagnosis code, and days since first dispensing the particular drug. In one example, filters established by the user may be saved for later use or modification.

In FIG. 5, the drug to be examined as well as the comparator drugs can be selected by the user. For instance, a list of available drugs for use as the comparator drug can be provided in one example.

Upon having selected the new drug and the comparator drug, a user may then select the type of report the user is interested in generating. FIG. 6 illustrates an example display screen wherein a plurality of standard report types are illustrated. If desired, the user may select a report showing, for the drug/comparator drug, the demographic characteristics, prevalence of diagnosis, prevalence of procedures, prevalence of drug class, healthcare utilization, characteristics of the prescribing parties, treatments that the drug has been used for, medical conditions among the drug, procedures among the drug, drug class dispensing, health care utilization among the drug, and clustered outcome for the drug.

Further, if desired, the user may be provided with the ability to create filtered views or data mining of an outcome from a standard report, such as where other parameters may be filtered from or focused in upon using the results of a standard report (see FIG. 8 below).

Figure 7:
FIG. 7 illustrates an exemplary computer display screen providing a tabular report view in accordance with one embodiment of the present invention.

FIG. 7 illustrates an example display screen of a tabular report view showing an example of how demographic characteristics of a drug or comparator drug can be displayed. For the new drug under examination, the number of data points is displayed and the demographics of the uses of the drug based on healthcare claims data may be displayed, including the age of the patients, gender, and geographic region. A similar display may be utilized for the comparator drug.

Patient data may specifically be made available so that the user may view the manner in which the test data or the comparator drug was actually utilized in medical treatment.

FIG. 8 illustrates an example display screen relating to filter parameters. Various filter parameters may be provided so that a user can apply a filter to the results of a standard report. For instance, in one example, filter parameters may include the drug type, patient age, patient gender, diagnosis code, and the number of days since first dispensing the particular drug. An "apply" but may be utilized so that once the user selects the particular filter, the filter may be applied to the results previously generated by the standard report. In this way, the user may, if desired, filter out certain parameters in order to better isolate the data of interest.

For instance, if the user is interested in the effect of a particular drug on infants six months old or younger, the user could utilize the age filter to filter out any patient data relating to patients whose age is greater than six months old. The filters which are created by the user and their resultants report data may be saved in a file for later reference.

FIGS. 9A and 9B illustrate an exemplary display screen relating to data mining. FIG. 9B illustrates the same chart as FIG. 9A, but the display in FIG. 9B is shifted to the right to show the final column of the chart illustrated in FIGS. 9A and 9B. The values shown in FIGS. 9A and 9B are as follows:

$X_d$=number of emergent events among matched NME initiators $N_d$=number of matched NME initiators $x_c$=number of emergent events among matched comparator drug initiators $N_c$=number of matched comparator drug initiators $$X_d + x_c = x \text{ (total number of emergent events)}$$

$$N_c + N_d = N \text{ (total number of matched NME and comparator drug initiators)}$$

Calculations are performed as follows:

$$RR = (xd/Nd)/(xc/Nc)$$

95% Confidence Interval (CI):
Lower Boundary:

$$Pd = (x_d - 0.5)/x$$

$$D = (1.96)^2/x$$

$$A = 1 + D$$

$$B = -2 * P_d - D$$

$$C = (P_d)2$$

$$P_{lower} = (-B - SQRT(B^2 - 4*A*C))/(2*A)$$

$$RR_{lower} = (P_{lower} * x/N_d)/((x - P_{lower} * x)/N_c)$$

However, if RR=0, then $RR_{lower}=0$
Upper Boundary:

$$Pd = (x_d - 0.5)/x$$

$$D = (1.96)^2/x$$

$$A = 1 + D$$

$$B = -2*P_d - D$$

$$C = (P_d)^2$$

$$P_{upper} = (-B + SQRT(B^2 - 4*A*C))/(2*A)$$

$$RR_{upper} = (P_{upper}*x/N_d)/((x - P_{upper}*x)/N_c)$$

However, if RR=infinity, then $RR_{upper}$=infinity
Score:

If $x_d = x*N_d/N$, then score=0

If $X_d < x*N_d/N$, then score=$\log_{10}$(cumulative hypergeometric$(x_d, N_d, x, N)$)

If $X_d > x*N_d/N$, then score=$-\log_{10}$(cumulative hypergeometric$(x-x_d, N-N_d, x, N)$)

In FIGS. 9A and 9B, scores are truncated to integer values for presentation.

Hence, it can be seen that embodiments of the present invention provide various methods (as well as computer implementations) for early identification of drug safety concerns.

Embodiments of the invention can be embodied in a computer program product. It will be understood that a computer program product including features of the present invention may be created in a computer usable medium (such as a CD-ROM or other medium) having computer readable code embodied therein. The computer usable medium preferably contains a number of computer readable program code devices configured to cause a computer to affect the various functions required to carry out the invention, as herein described.

While the methods disclosed herein have been described and shown with reference to particular operations performed in a particular order, it will be understood that these operations may be combined, sub-divided, or re-ordered to form equivalent methods without departing from the teachings of the present invention. Accordingly, unless specifically indicated herein, the order and grouping of the operations is not a limitation of the present invention.

It should be appreciated that reference throughout this specification to "one embodiment" or "an embodiment" or "one example" or "an example" means that a particular feature, structure or characteristic described in connection with the embodiment may be included, if desired, in at least one embodiment of the present invention. Therefore, it should be appreciated that two or more references to "an embodiment" or "one embodiment" or "an alternative embodiment" or "one example" or "an example" in various portions of this specification are not necessarily all referring to the same embodiment. Furthermore, the particular features, structures or characteristics may be combined as desired in one or more embodiments of the invention.

It should be appreciated that in the foregoing description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed inventions require more features than are expressly recited in each claim. Rather, as the following claims reflect, inventive aspects lie in less than all features of a single foregoing disclosed embodiment, and each embodiment described herein may contain more than one inventive feature.

While the invention has been particularly shown and described with reference to embodiments thereof, it will be understood by those skilled in the art that various other changes in the form and details may be made without departing from the spirit and scope of the invention.

What is claimed is:

1. A computer-implemented system for administering a drug registry database, comprising:
    an electronic database containing a plurality of healthcare claims for a plurality of patients and a plurality of new drug/comparator drug pairings predefined by a system administrator;
    an electronic user interface configured to
        display the plurality of new drug/comparator drug pairings, wherein each new drug is added to the database when a threshold number of healthcare claims for the new drug have been received and wherein each comparator drug paired with a new drug that has substantially similar medical indications as the new drug; and
        receive a selection of a new drug/comparator drug pairing, and filter parameters input by a user; and
    a computer-implemented analysis engine configured to
        search the healthcare claims contained in the database to identify a first and second group of patients satisfying the filter parameters input by the user; wherein the first group includes patients with claim data indicating use of the new drug and the second group includes patients with claim data indicating use of the comparator drug;
        identify a comparative occurrence of one or more existing medical conditions or new medical conditions in the first and second groups of patients; and
        calculate a probability value indicating a relative likelihood that a patient taking the new drug will have each of the one or more new or existing medical conditions in comparison to a likelihood that a patient taking the comparator drug will have each of the one or more new or existing medical conditions;
    wherein the electronic user interface displays each new or existing medical condition and the probability value for the new drug and the comparator drug in accordance with one or more report parameters entered by the user.

2. The system according to claim 1, wherein the display generated by the electronic user interface includes demographic characteristics, prevalence of diagnosis, prevalence of procedures, prevalence of drug class, or healthcare utilization.

3. The system according to claim 1, wherein the filter parameters include one or more diagnosis codes, procedure codes, drug categories, or demographic characteristics.

4. A computer-implemented method for administering a drug registry database, comprising:
    storing in an electronic database a plurality of healthcare claims for a plurality of patients and a plurality of new drug/comparator drug pairings predefined by a system administrator;
    displaying on an electronic user interface a plurality of new drug/comparator drug pairings, wherein each new drug is added to the electronic database when a threshold number of healthcare claims for the new drug have been received and wherein each comparator drug paired with a new drug that has substantially similar medical indications as the new drug;
    receiving a selection of a new drug/comparator drug pairing, and filter parameters input by a user;
    searching the healthcare claims stored in the electronic database to identify a first and second group of patients satisfying the filter parameters input by the user; wherein the first group includes patients with claim data indicating use of the new drug and the second group includes patients with claim data indicating use of the comparator drug;

identifying a comparative occurrence of one or more existing medical conditions or new medical conditions in the first and second groups of patients;

calculating a probability value indicating a relative likelihood that a patient taking the new drug will have each of the one or more new or existing medical conditions in comparison to a likelihood that a patient taking the comparator drug will have each of the one or more new or existing medical conditions; and displaying each new or existing medical condition and the probability value for the new drug and the comparator drug in accordance with one or more report parameters entered by the user on the electronic user interface.

5. The method according to claim 4, wherein the display generated by the user interface includes demographic characteristics, prevalence of diagnosis, prevalence of procedures, prevalence of drug class, or healthcare utilization.

6. The method according to claim 4, wherein the filter parameters include one or more diagnosis codes, procedure codes, drug categories, or demographic characteristics.

* * * * *